United States Patent [19]
Messner et al.

[11] Patent Number: 5,999,837
[45] Date of Patent: Dec. 7, 1999

[54] LOCALIZING AND ORIENTING PROBE FOR VIEW DEVICES

[75] Inventors: Dale A. Messner, Uniontown; John D. Schellenberg, Cleveland Heights; Patrick A. Dayton, Munroe Falls, all of Ohio

[73] Assignee: Picker International, Inc., Cleveland, Ohio

[21] Appl. No.: 08/938,209

[22] Filed: Sep. 26, 1997

[51] Int. Cl.⁶ .................................................... A61B 6/00
[52] U.S. Cl. ........................ 600/407; 600/417; 600/420
[58] Field of Search ................................... 600/407, 415, 600/424; 606/130; 359/368

[56] References Cited

U.S. PATENT DOCUMENTS

| | | |
|---|---|---|
| 4,722,056 | 1/1988 | Roberts et al. . |
| 5,162,641 | 11/1992 | Fountain . |
| 5,286,964 | 2/1994 | Fountain . |
| 5,383,454 | 1/1995 | Bucholz . |
| 5,513,005 | 4/1996 | Müller et al. . |
| 5,517,990 | 5/1996 | Kalfas et al. . |
| 5,867,308 | 2/1999 | Pensel et al. ............................ 359/368 |
| 5,904,691 | 5/1999 | Barnett et al. . |

OTHER PUBLICATIONS

"A Frameless Stereotaxic Operating Microscope for Neurosurgery", Eric M. Friets, et al.; IEEE Transactions on Biomedical Engineering, vol. 36, No. 6, Jun. 1989 pp. 608–617.

"A frameless stereotaxic integration of computerized tomographic imaging and the operating microscope", David W. Roberts, M.D., et al.; J. Neurosurg, vol. 65; Oct. 1986; pp. 545–549.

*Primary Examiner*—Marvin M. Lateef
*Assistant Examiner*—Ali M. Imam
*Attorney, Agent, or Firm*—Timothy B. Gurin; John J. Fry; Eugene E. Clair

[57] ABSTRACT

A microscope calibrator probe includes a handle, a tool head connected to the handle, a viewable target connected to an end of the tool head opposite the handle, and three or more position signaling devices disposed on the handle for tracking the probe in an image guided surgery system. The tool head includes a bend of approximately 90 degrees to provide easy placement of the viewable target on an object being viewed below a microscope. Other angles for the bend are also acceptable. A precise location of the object being viewed is determined by sensing a location the three or more position signaling devices disposed on the handle with respect to an operating room reference frame and knowing an offset between the position signaling devices and a bottom surface of the viewable target in contact with the object. Additionally, the viewable target includes a viewable aperture for calibrating a line of sight of the microscope and a means for indicating a rotational sense of the viewable target.

30 Claims, 4 Drawing Sheets

LOCALIZING AND ORIENTING PROBE FOR VIEW DEVICES

TECHNICAL FIELD

The present invention relates to the medical diagnostic and surgical arts. More particularly the present invention relates to a microscope calibrator probe for calibrating and verifying calibration of a microscope used in conjunction with various medical procedures including neurosurgery, neurobiopsy, CT-table needle body biopsy, breast biopsy, endoscopic procedures, orthopedic surgery, and the like.

BACKGROUND OF THE INVENTION

Three-dimensional diagnostic images of the brain, spinal cord, and other body portions are produced by diagnostic imaging equipment such as CT scanners, magnetic resonance imagers, and the like. These imaging modalities often provide structural detail with a resolution of a millimeter or better.

Image guided surgery systems have been developed to utilize this data to assist the surgeon in presurgical planning and in accurately locating a region of interest within the body of a patient. In the operating arena, the image guided surgery systems are used to display position and orientation of a surgical tool in its correct location with respect to the images of the patient. One example of an image guided surgery system is U.S. Pat. No. 5,517,990, Stereotaxy Wand and Tool Guide, to Kalfas et al. issued May 21, 1996, incorporated by reference herein.

In order to further aid the surgeon in viewing an area of interest within the patient's body, a high powered surgical microscope is often utilized. Such a microscope may, for instance, be used to see blood vessels or other microscopic details within the patient. The microscope is supported by a movable electronic support structure which may be rolled along the ground or mounted to a ceiling or a wall, for example. Controls adjacent the microscope on the support structure allow the surgeon to manually or electronically position the microscope over the patient's body at a desired location.

In order to track the location of the microscope within the surgical room or other area, a series of position signaling devices such as infrared emitters or reflectors are typically secured to the microscope at some location. The position signaling devices are tracked by a localizer located within the surgical room capable of sensing the position signaling devices. The image guided surgery system uses this data to provide the surgeon with an indication of the position and orientation of the microscope with respect to patient data and images.

Unfortunately, calibrating views seen through a microscope with respect to images displayed on a monitor is often a nuisance. For instance, often times a surgeon is able to find a region of interest without aid of a monitor tracking the position of the microscope and thus the surgeon would prefer if he or she were able to simply verify a location and orientation of the microscope once the region of interest is sighted. Further, in situations where a microscope is not tracked by virtue of position signaling devices, determining the precise positioning of an object in view with respect to images shown on the monitor becomes extemely difficult.

The present invention provides a new and improved method and apparatus for calibrating and verifying calibration of a surgical microscope which addresses the above-referenced matters, and others.

SUMMARY OF THE INVENTION

A microscope calibrator probe includes a handle, a tool head connected to the handle, a viewable target connected to an end of the tool head opposite the handle, and three or more position signaling devices disposed on the handle for tracking the probe in an image guided surgery system.

In a preferred embodiment, the handle includes three or more position signaling devices on each of a front side and rear side of the handle to accommodate both right and left handed users. Further, the tool head includes a bend of approximately 90 degrees to provide easy placement of the viewable target on an object being viewed below a microscope. Other angles for the bend are also acceptable.

A precise location of the object being viewed is determined by sensing a location the three or more position signaling devices disposed on the handle with respect to the operating room and knowing an offset between the position signaling devices and a bottom surface of the viewable target in contact with the object. The viewable target also includes a viewing aperture for calibrating a line of sight of the microscope. More specifically, by aligning the microscope with an axis of the viewable aperture such that a clear, unobstructed view through the viewable aperture is achieved, a position of the probe can be sensed and translated to a current line of sight of the microscope. Additionally, the viewable target also may include a means for indicating a rotational sense of the viewable target. For example, the means for indicating may be a marking on a top face of the viewable target. The means for indicating the rotational sense is aligned with a view through the microscope to allow a surgeon to set a desired rotational sense of the microscope with respect to images shown on monitors.

In accordance with the present invention, An apparatus for determining an attribute of a microscope is provided. The apparatus including a target alignable along a focal axis of the microscope, and a plurality of position signaling devices having a known relationship to the target.

In accordance with another aspect of the present invention, a system for determining an attribute of a microscope is provided. The system including a tool, a means for tracking the plurality of position signaling devices, and a means for processing information tracked by the means for tracking. The tool includes a tool head, a means for supporting the tool head, a viewable target coupled to an end of the tool head, and a plurality of position signaling devices having a known relationship to the viewable target.

In accordance with still another aspect of the present invention, a method of determining an attribute of a microscope is provided. The method includes the steps of focusing the microscope on an object in a field of view of the microscope, positioning a target on the object in the field of view, and sensing the position of the target in relation to the microscope.

In accordance with yet another aspect of the present invention, a method of determining an attribute of a microscope in an image guided surgery system is provided. The method includes the steps of focusing the microscope on a viewable target which has a means for indicating a rotational sense of the viewable target, positioning the viewable target such that the means for indicating the rotational sense of the viewable target is aligned with a desired rotational sense of the microscope, and using the image guided surgery system to determine a position of the position signaling device.

It is an object of the present invention to provide a means for quickly determining or verifying a focusing distance of a surgical microscope.

It is another object of the present invention to provide a means for easily determining or verifying a line of sight of a surgical microscope.

It is still another object of the present invention to provide a means for determining an exact location of an object being viewed through a surgical microscope.

It is yet another object of the present invention to provide a means for calibrating a rotational sense of the surgical microscope.

It is yet another object of the present invention to provide a device capable of determining or verifying a location, line of sight, and rotational sense of the surgical microscope independent of whether the microscope is tracked.

To the accomplishment of the foregoing and related ends, the invention then, comprises the features hereinafter fully described and particularly pointed out in the claims. The following description and the annexed drawings set forth in detail certain illustrative embodiment of the invention. These embodiments are indicative, however, of but a few of the various ways in which the principles of the invention may be employed. Other objects, advantages and novel features of the invention will become apparent from the following detailed description of the invention when considered in conjunction with the drawings.

DETAILED DESCRIPTION OF THE PREFERRED EMBODIMENTS

Figure 1:
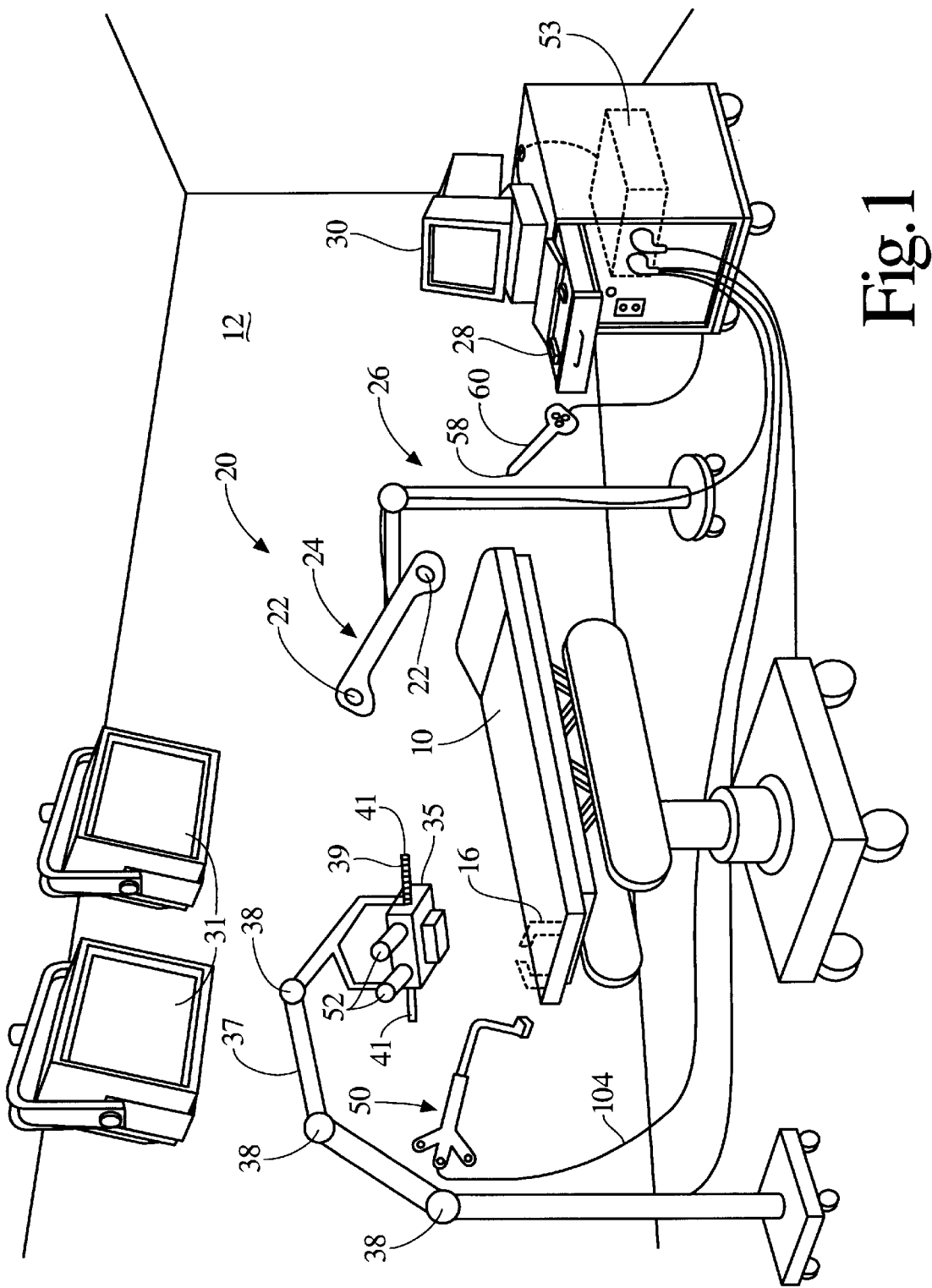
FIG. 1 is a perspective view of an operating room in which the present invention is deployed.

The present invention will now be described with reference to the drawings in which like reference numerals are used to refer to like elements throughout.

With reference to FIG. 1, a patient (not shown) is received on an operating table or other subject support 10 and appropriately positioned within an operating or surgical room 12. A securing means such as a head clamp 16 securely positions a portion of the patient or subject under consideration. A locating device 20 such as an infrared localizer determines the location and orientation of at least one surgical tool. Tools refers to any instrument or apparatus in the surgical room which is tracked by the locating device 20.

In the preferred embodiment, the locating device 20 is an infrared localizer such as the Polaris™ localizer system supplied by Northern Digital, Inc. of Waterloo, Ontario, Canada. The localizer system includes two spaced apart infrared cameras 22 mounted on a sensor head 24. The sensor head 24 is in turn mounted in a fixed position within the operating room 12, for example on a stand 26 resting on the floor. The cameras 22 may be mounted in another known position in the operating room 12, such as to the ceiling or wall or to the subject support 10. Of course, other locating devices, such as ultrasonic, optical, RF, or electromagnetic localizers, may be used. The surgical tool may also be mounted to an articulated arm, the arm functioning as the locating device.

A surgical microscope 35 aids a surgeon in viewing microscopic images of the patient while conducting a procedure or surgery. The surgeon views the images through a viewing piece 52 of the microscope 35. The viewing piece 52 may include cross hairs or other markings to aid the surgeon with calibrating a rotational sense of the microscope 35 with respect to images shown on monitors such as overhead monitors 31. The microscope 35 is supported by a microscope support structure 37 which is situated on the floor. The microscope support structure 37 includes several movable joints 38 which may be manually or electronically controlled to position the microscope 35 in a desired location. For instance, control buttons 39 attached to a handle 41 of the microscope 35 may be used to accurately and precisely locate the microscope 35 in the operating room 12. A reference frame target (not shown) including three or more position signaling device is rigidly attached to the microscope 35. The position signaling devices may, for instance, be infrared emitters, sonic emitters, RF emitters, or reflectors depending on the type of locating device 20 in the operating room 12. The reference frame target provides a means for the locating device 20 to accurately track a positioning of the microscope 35 with respect to the operating room 12. Although the microscope support structure 37 is shown to be situated on the ground, it will be appreciated that the microscope support structure could alternatively be attached to the ceiling or to a wall. Of course, the microscope 35 could be supported by any other suitable mechanism. The microscope 35 may be designed to have a fixed or variable focal distance. In the event the focal distance is fixed, the microscope 35 must be physically positioned by the surgeon to focus in on an object of interest. In the event the focal distance is variable, the surgeon may be able to keep the microscope 35 fixed in a physical location, while varying the focusing distance of a microscope lens to a desired distance. In instances where the focusing distance is variable, it will be appreciated that the focusing distance of the microscope 35 may be precalibrated and the microscope 35 may come equipped with a signaling device or other means for indicating to the surgeon the current focusing distance of the microscope lens.

A surgical microscope calibrator probe 50 is located in the operating room 12. As will be discussed in more detail below, the microscope calibrator probe 50 provides a means for rapidly and accurately calibrating and verifying the calibration of the microscope 35.

Figure 2:
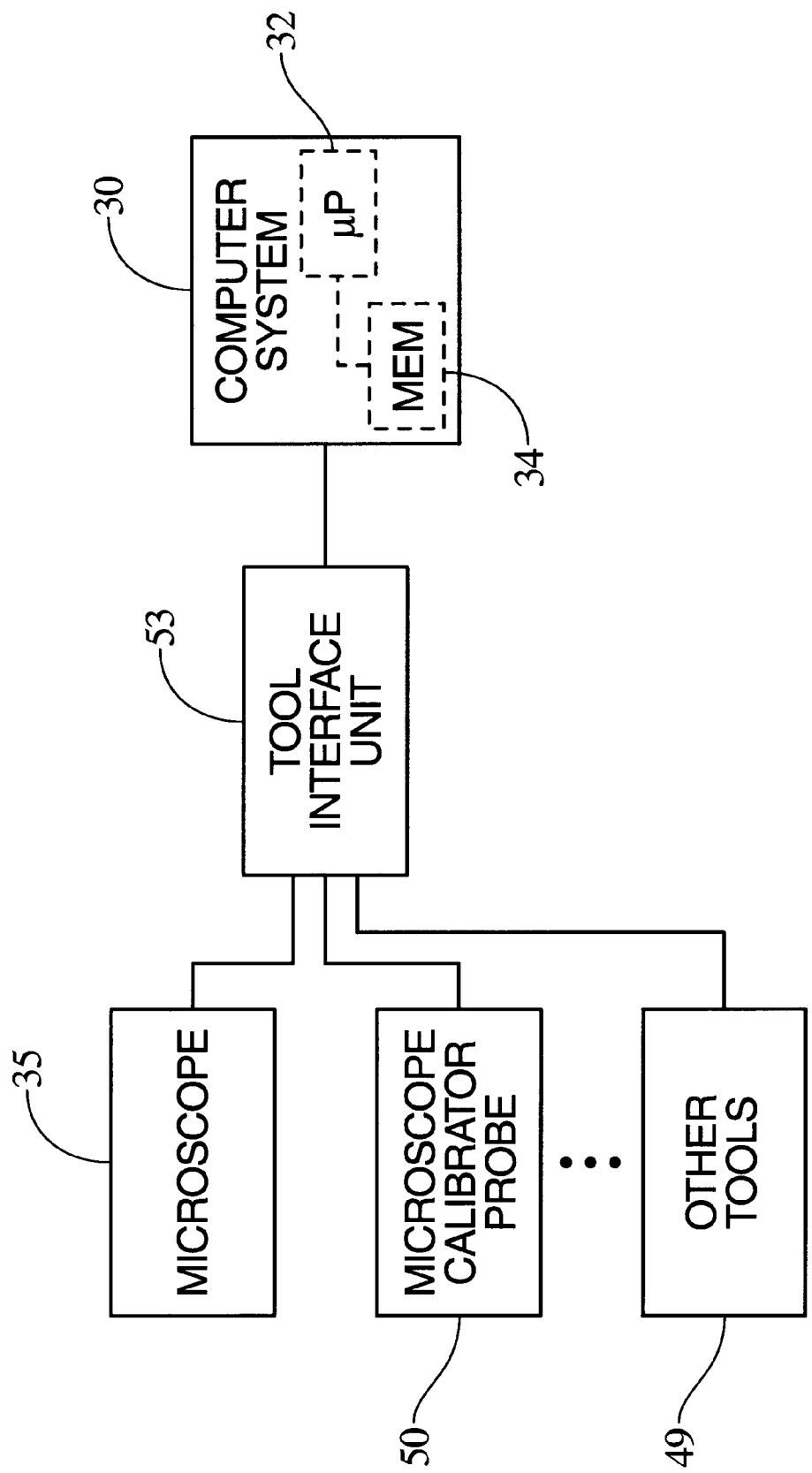
FIG. 2 is a block diagram of a system according to the present invention.

With continued reference to FIG. 1 and further reference to FIG. 2, an operator console 28 supports a computer system 30. Alternately, the computer system 30 can be remotely located and connected with the operator console 28 by cabling. The computer system 30 includes a processor 32 and a data memory 34 coupled to the processor 32. The data memory 34 contains data indicative of a three-dimensional image of the patient or subject. Because the data can be visualized as a three-dimensional rectangular grid, selectable orthogonal and other oblique planes of the data can be readily withdrawn from the data memory 34 using conventional technology. Such data may be displayed on the overhead monitor 31 in the operating room 12 for convenient viewing by the surgeon.

The microscope 35, the microscope calibrator probe 50, and other tools 49 are coupled to the computer system 30 through a tool interface unit 53. The tool interface unit 53 serves to interface the computer system 30 with all the tools in the operating room 12.

Each tool in the operating room passes along information related to its local reference frame to the tool interface unit 53. For instance, the local reference frame for the microscope calibrator probe 50 may be defined such that an origin is at some desirable location associated with the microscope calibrator probe 50. Based on signals detected by the cameras 22, the location and orientation of the microscope calibrator probe 50 and hence the local reference frame with respect to the cameras 22 and hence the operating room reference frame are determined. Similarly, the relationship between the local reference frames of the other tools and the operating room reference frame may be determined.

As is well known in the art, transforms between the patient, tools and operating room reference frames can readily be calculated. A transform is accomplished by determining an offset $x_{offset}$, $y_{offset}$, $z_{offset}$ between the reference frames to be transformed. These values of $x_{offset}$, $y_{offset}$, $z_{offset}$ are added to or subtracted from the coordinates of one of the reference frames as required to translate between the two. The coordinate systems are then rotated relative to each other about their origins by angles $\alpha$, $\beta$, $\gamma$ so that their respective x, y and z axes coincide.

Figure 3:
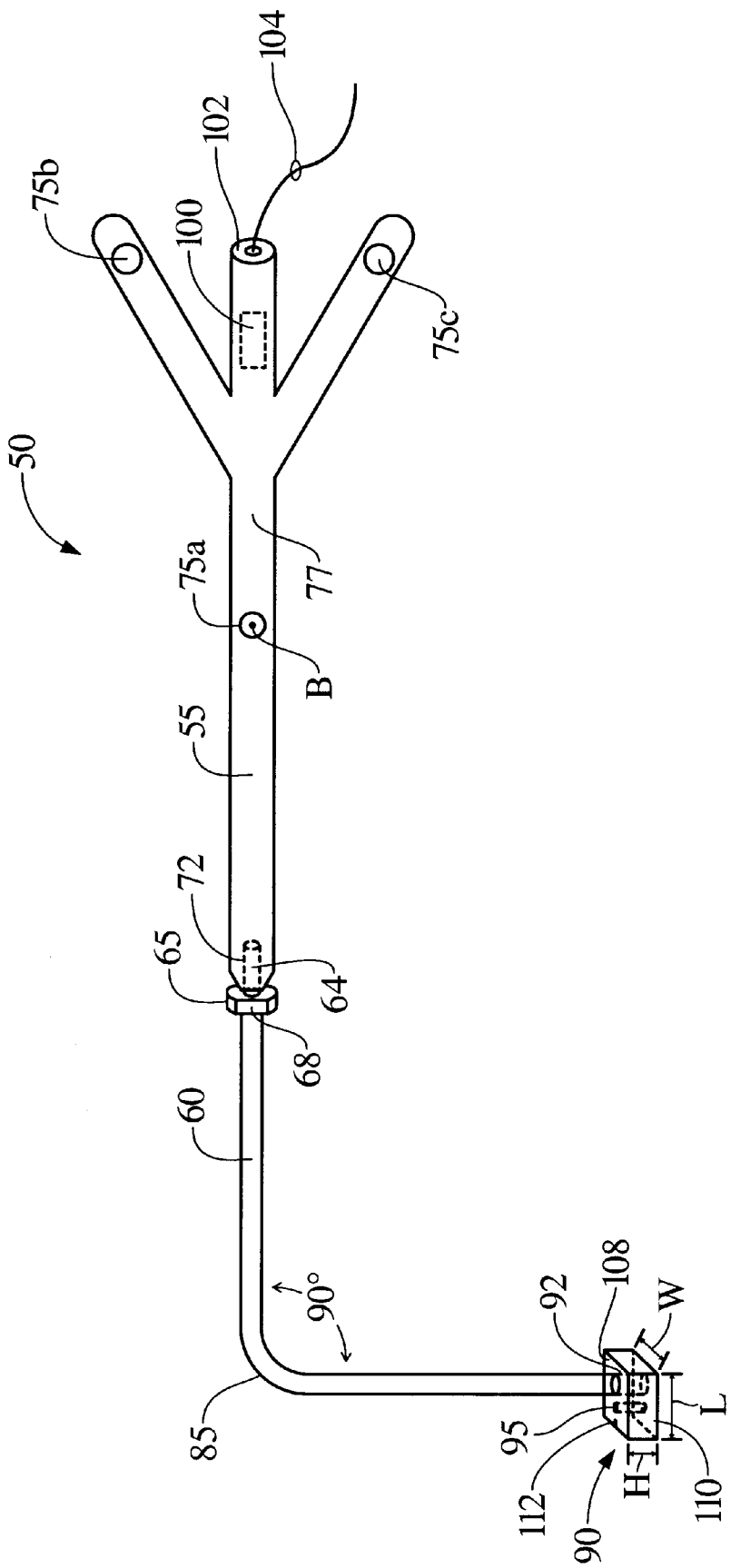
FIG. 3 is a front view of a microscope calibrator probe of the present invention.
Figure 4:
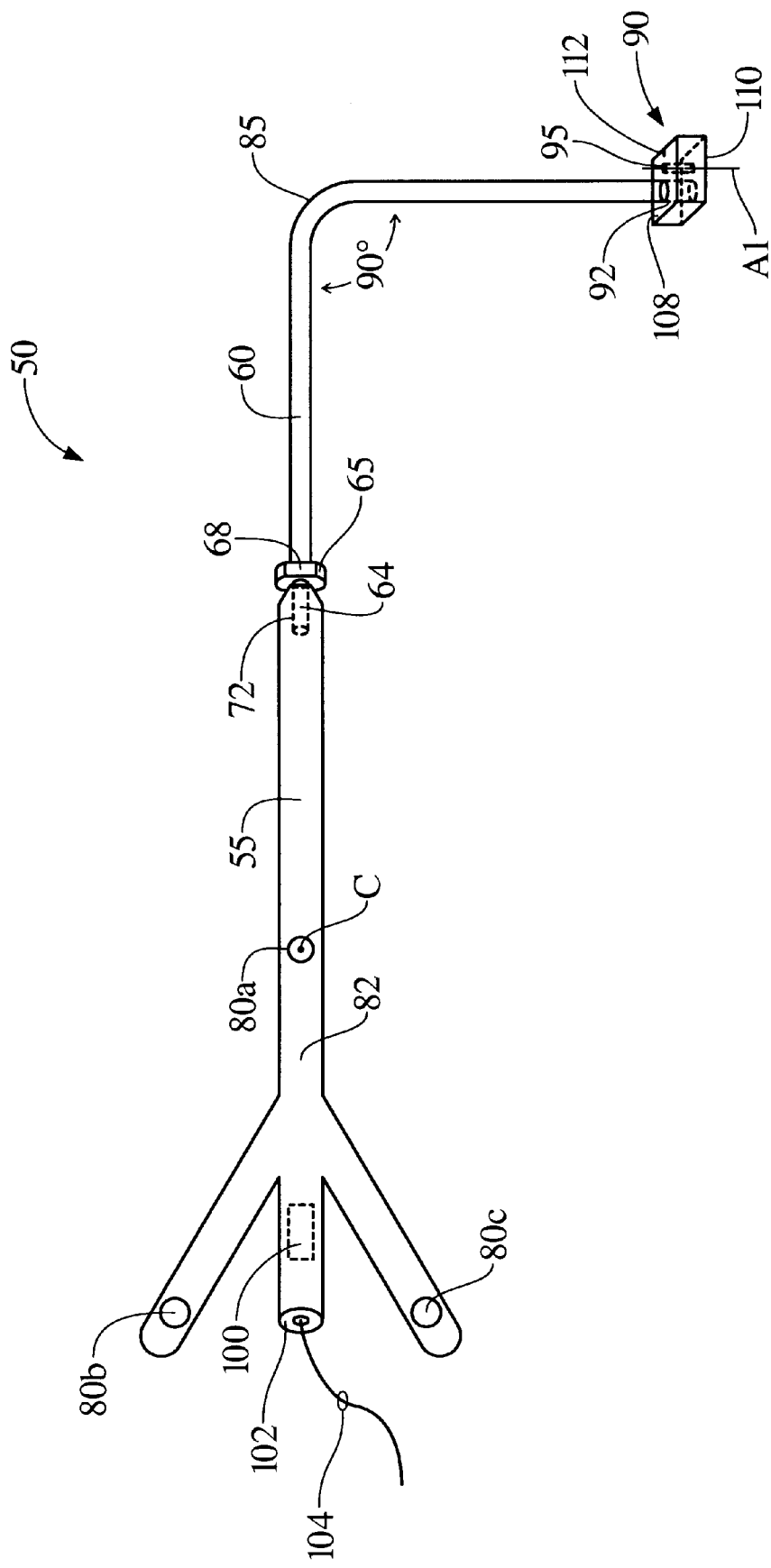
FIG. 4 is a back view of the microscope calibrator probe of FIG. 3.

Referring now to FIGS. 3 and 4, the microscope calibrator probe 50 of the preferred embodiment is shown in more detail. The microscope calibrator probe 50 includes a handle 55 and a tool head which in the present embodiment is shaft 60. An end of the shaft 60 closest the handle 55 includes a threaded connector 64 and screw head 65 for securing the shaft 60 to the handle 55. The screw head 65 is shaped with a two or more flat sides 68 to allow a wrench or other tool to aid in securing the threaded connector 64 to the handle 55. An end of the handle 55 closest the shaft 60 includes a corresponding threaded aperture 72 for receiving the screw head 64. The threaded aperture 72 is sized to ensure a secure threaded fit is made with the threaded connector 64. Glue or other adhesive material may be provided within the threaded aperture 72 to aid in securing the shaft 60 to the handle 55 in a desirable position.

The handle 55 includes a series of position signaling devices 75a, 75b, 75c, collectively referred to as position signaling devices 75, disposed on a front side 77 of the probe 50 as shown in FIG. 3. The handle 55 also includes a series of position signaling devices 80a, 80b, 80c, collectively referred to as position signaling devices 80, disposed on a rear side 82 of the probe 50 as shown in FIG. 4. The location of position signaling devices 75 and position signaling devices 80 are such that planes defined by each of the respective position signaling devices 75, 80 are substantially parallel to one another. The position signaling devices 75, 80 of the preferred embodiment are infrared emitters such as light emitting diodes. However, it will be appreciated that other position signaling devices such as reflectors, sonic emitters, and RF emitters could alternatively be used. It will also be appreciated that additional position signaling devices could be used to serve as a backup in the event one or more of the existing position signaling devices 75,80 fail or become out of sight or range of the cameras 22.

As seen in FIGS. 3 and 4, the shaft 60 includes a bend 85 and a viewable target 90 connected to an end of the shaft 60 furthest from the handle 55. The bend 85 in the present embodiment is shown to be at a 90 degree angle, although any suitable angle, or no angle at all, could be selected.

The target 90 includes an aperture 92 for receiving and rigidly securing to the shaft 60. More specifically, a diameter of the aperture 92 is such that the shaft 60 frictionally press fits within the aperture thereby providing a non-rotating, rigid connection between the shaft 60 and the target 90.

Referring now to FIG. 3, the target is shown to be rectangular in shape and has dimensions of a height H, width W and length L. The length L and width W of the target 90 are sized so that the target can readily be inserted into relatively small areas being viewed within the patient through the microscope 25. In the present embodiment, the length L is 8 mm and the width W is 6 mm. The height H of the target 90 is also relatively small in size so as to fit within small regions being viewed, however is tall enough to ensure that a line of sight of the microscope 35 may be properly calibrated as is discussed in more detail below. In the present embodiment, the height is 6 mm. It will be appreciated that although the target 90 of the present embodiment is rectangular in shape, the target 90 could take any shape. For instance, the target 90 could be spherical, triangular, hexagonal, cylindrical, oval, etc.

Referring again to FIGS. 3 and 4, the target 90 is shown to include a viewing aperture 95 which defines a viewing axis A1. The viewing axis A1 (FIG. 4) of the viewing aperture 95 is substantially parallel to the planes formed by the position signaling devices 75 and the position signaling devices 80. The viewing aperture 95 of the present embodiment has a diameter of 2 mm, however any suitable size aperture may be selected as is discussed in more detail below. The target further includes a top surface 108 and a bottom surface 110. Planes defined by both the top surface 108 and bottom surface 110 are substantially orthogonal to the axis A1 and to the planes defined by the position signaling devices 75, 80, respectively. The target 90 includes a means for indicating a rotational sense of the target 90. In the present embodiment, the means for indicating the rotational sense of the target is an indicator mark 112 drawn on the top surface 108 of the target 90. Other means for indicating a rotational sense, such as placing a notch on the top surface 108 of the target 90 or shaping the target 90 to have a pointed edge, etc. could also be used. In the present embodiment, the target is made of stainless steel, however, it will be appreciated that any other durable material including, but not limited to, plastic, wood, rubber, and other metals could be used.

A memory 100 disposed in the handle 53 couples to the tool interface unit 55 via a seven pin female connector 102 and cord 104. The memory 100 stores and supplies the tool interface unit 53 with information related to the positioning of the position signaling devices 75, 80 with respect to the local reference frame of the probe. Further, the memory 100 stores and supplies to the tool interface unit 53 a three dimensional offset between the plane defined by a bottom surface 108 of the target 90 and a selected point with respect to each of the position signaling devices 75, 80. The selected points of the present embodiment are points B and C located at a center of position signaling devices 75a, 80a, respectively (see FIGS. 3 and 4). It will be appreciated, however, that any point could have been selected. Further, it is additionally and alternatively possible to store in the memory 100 a location of a top surface 108 of the target with respect to points B and C. As can be seen, once a location of either the top surface 108 or bottom surface 108 is known, the location of the other can be readily calculated based on knowing the height H of the target 90. The memory 100 also stores offset values between points B and C and the axis A1 of the viewing aperture 95.

Determining attributes of the microscope 35 includes calibrating or determining a focusing distance of the microscope lens such that a center of a depth of field can be determined, calibrating or determining a rotational sense of the microscope such that images seen at the top, bottom, left and right of the microscope viewing field correspond to the orientation of an image on the viewable monitor, and calibrating or determining a line of sight or barrel sight of the microscope with respect to the surgical room. The microscope calibrator probe 50 of the present invention is able to calibrate, determine and verify calibration of the microscope 35 with respect to any and all of the above in a simple and easy manner.

In operation, a surgeon initially situates the microscope 35 above a region to be viewed and focuses the microscope on an object of interest. Often times the surgeon is able to locate the object of interest with the microscope without aid of the image guided surgery system. Thus, precalibrating the microscope 35 using a known calibration method is not always necessary. Once the object of interest is located and clearly focused upon by the surgeon, the surgeon places the bottom surface 108 of the target 90 of the microscope calibrator probe 50 on top of the object. As the shaft 60 of the probe 50 includes bend 85, the surgeon is typically able to reach the object without obstructing a view from the microscope 35 or otherwise needing to reorient the microscope 35 with respect to the object. If the shaft 60 did not include the bend 85, it would likely be difficult to position the target 90 to the desired location as the handle 55 of the probe 50 would not easily fit underneath the microscope 35 while still being able to focus the microscope 35 on the object. Once the bottom surface 110 of the target 90 is situated on the object, the surgeon is able to calibrate the focusing distance of the microscope 35. More specifically, by entering a calibrate command to the computer system 30, the cameras 22 sense a location of the probe 50 through position signaling devices 75 or 80, whichever is in a line of sight with the camera 22. Next, using stored offset information between the position signaling devices 78 and 80 as stored in memory 100, the computer system 30 determines the location of the bottom surface 110 of the target 90 with respect to the operating room. Using this information, a distance between a point intersecting axis A1 on the bottom surface 110 of the target 90 and a sensed location of the microscope 35 is determined. Based on this information, an approximate location in which the microscope 35 is currently focused is determined and the focusing distance of the microscope 35 is calibrated. If an exact location in which the microscope 35 is currently focused is desired, the user must ensure that the object of interest underneath the target 90 is also intersected by the axis A1 of the viewing aperture 95. This may, for instance, be accomplished by viewing the object through the aperture 95 with the microscope 35 prior to calibrating the location of the object.

Once the target has been placed on top of the object of interest, the surgeon may optionally calibrate or verify a line of sight of the microscope 35. Calibration of the line of sight is accomplished by viewing the object through the viewing aperture 95 of target 90. More specifically, the surgeon positions the probe 50 until he or she is able to see directly down the axis A1 of the viewing aperture 95. The surgeon is able to determine if alignment of the microscope 35 and the viewing aperture 95 is properly made by determining whether any part of an inner wall of the viewing aperture 95 is seen through the microscope 35. If portions of the inner wall of the viewing aperture 95 are seen, the surgeon must realign the probe 35 until a clear, unobstructed view of the object through the viewing aperture 95 is visible. Once proper alignment is made, the surgeon or other individual inputs a command to the computer system 30 to calibrate the line of sight of the microscope 35. Based on the sensed position of the microscope 35 and the probe 50, the current line of sight of the microscope 35 is calibrated. A diameter of the viewing aperture 95 and height of the target should be sized to accommodate the magnification power of microscope 35 being calibrated. If, for instance, very slight movements of the target cause complete loss of view through the viewing aperture, the diameter of the viewing aperture 95 should be increased or height H of the target 90 should be reduced to accommodate such slight human movements in handling the probe 50.

It will be appreciated, that in some instances the microscope 35 may not include position signaling devices attached thereto and thus is not tracked in the operating room. In such circumstances, the present invention nevertheless provides a manner in which both the exact focusing distance of the microscope and the line of sight of the microscope may be calibrated at any given location.

A rotational sense of the microscope 35 may also be optionally calibrated or verified with use of the probe 50. To calibrate or verify the rotational sense of the microscope 35, the surgeon aligns the indicator mark 112 on target 90 with a desired marking (such as a top cross hair) seen through the viewing piece 52 (FIG. 1) of the microscope 35. Once the indicator mark 112 on the target 90 is aligned with the desired marking seen through the viewing piece 52, the surgeon or other individual inputs a command to the computer system 30 indicating that a rotational sense of the microscope 35 is being calibrated. The direction in which the indicator mark 112 is pointing with respect to the operating room 12 is taken to be a top direction for an image displayed on a monitor such as overhead monitors 31. Based on the sensed location of the microscope 35, the displayed images may later be rotated in conjunction with sensed movements of the microscope 35 in the operating room 12. The probe 50 may also be used independent of the microscope 35 to indicate to the computer system 30 which portion of an image the surgeon prefers to have at the top of the viewable monitors 31. For instance, if a patients head is currently displayed on the monitors 31 with a top portion of the head situated at the top of the viewable monitor 31, the surgeon may point the top indicator mark 112 of the probe 50 to the left or right of the patient's body and enter a command to the computer system 30 to rotate the image on the screen by 90 degrees. It is, of course, possible to do some or all of the above calibrations simultaneously and enter a single command to the computer system 30.

It will be appreciated that the position and orientation of the position signaling devices 75, 80 of the present invention serve several purposes. One reason for providing position signaling devices 75, 80 on both the front side 77 and back side 82 of the probe is to accommodate both left and right handed individuals. Additionally, having position signaling devices 75, 80 on both sides of the probe 50 allows more flexibility in using the probe 50 without worry of losing a line of sight between the probe 50 and cameras 22. Because the planes defined by each of the position signaling devices 75, 80 are substantially parallel and the position signaling devices 75,80 are facing opposite directions, the cameras 22 tracking the probe 50 only sense one of the two position signaling devices 75,80 at any given time. Further, because the planes defined by the position signaling device 75, 80 are substantially parallel to the viewing axis A1 and, in the preferred embodiment, substantially orthogonal to the planes defined by the top surface 108 and bottom surface 110 of the target 90, it is likely that a line of sight between one of the position signaling devices 75 or 80 and the cameras 22 is not obstructed when the target 90 is on the object being viewed through the microscope 35. If for instance, the planes defined by the position signaling devices 75 and 80 were rotated such that they were orthogonal to the viewing axis A1, then in most circumstances when the target 90 is placed on the object one set of the position signaling devices 75 or 80 would face the ceiling while the other set of the position signaling devices 78 or 80 would face downward towards the object of interest. Unfortunately, as the cameras 22 are not typically located on the ceiling or directly above the object being viewed by the microscope 35 but rather at some location surrounding the patient, it is preferable to not to have the position signaling devices orientated in this manner.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or their equivalence thereof.

What is claimed is:

1. An apparatus for use with a surgical microscope, the apparatus comprising:
   a target for placement on an object of interest in known relationship with a focal axis of the surgical microscope, the target including means, when viewed through the microscope, for providing a visual indication when the visual indication providing means is in alignment with the focal axis of the microscope; and
   means for communicating signals indicative of the location of the target.

2. The apparatus of claim 1 wherein the means for communicating the location of the target includes a position indicator having a known location with respect to the target.

3. The apparatus of claim 2 wherein the position indicator includes a plurality of infrared emitters.

4. The apparatus of claim 2 wherein the position indicator includes a plurality of passive devices.

5. The apparatus of claim 2 wherein the position indicator is disposed on a first surface of a support assembly associated with the target.

6. The apparatus of claim 5 including a second surface of the support assembly and the position indicator is mounted to the support assembly in a manner to communicate the position of the target from both the first and second surfaces of the support assembly.

7. The apparatus of claim 5 wherein the support assembly includes a handle to which the position indicators are mounted.

8. The apparatus of claim 7 wherein a tool head is attached between the target and the handle.

9. The apparatus of claim 8 wherein the tool head comprises a shaft with a bend.

10. The apparatus of claim 9 wherein the bend is substantially 90 degrees.

11. The apparatus of claim 1 wherein the target includes a second surface opposite the first surface, a material free region extending through the target from the first surface to second surface wherein the configuration of the material free region is adapted for aligning the target along the focal axis of microscope.

12. The apparatus of claim 11 wherein the means for communicating defines a plane and an axis of the material free region is substantially parallel with the plane.

13. The apparatus of claim 12 wherein the contact surface is substantially orthogonal to the plane.

14. The apparatus of claim 11 wherein the material free region is an aperture in the target.

15. The apparatus of claim 14 wherein the size of the aperture is adapted to accommodate the magnification power of the microscope.

16. The apparatus of claim 1 wherein the signals indicative of the location of the target includes signals indicative of at least one of the distance of the contact surface from the surgical microscope, the alignment of the target with the focal axis of the surgical microscope and the rotational orientation of the target with respect to the surgical microscope.

17. The apparatus of claim 16 wherein the rotational orientation of the target is indicated by a mark on the target.

18. A system for determining an attribute of a microscope, the system comprising:
   a tool including:
      a target for placement on an object of interest in known relationship with a focal axis of the microscope, the target including a material free region adapted to provide a visual indication when viewed through the microscope when the target is in said known relationship to said focal axis of the surgical microscope;
      means for supporting the target; and
      a plurality of position signaling devices having a known relationship to the target;
   means for tracking the plurality of position signaling devices; and
   means for processing information tracked by the means for tracking.

19. The system according to claim 18, wherein the means for supporting the target is a tool head.

20. The system according to claim 19, comprising at least three position signaling devices disposed on a first surface of the handle.

21. The system according to claim 20, wherein the tool head includes a bend.

22. The system according to claim 21, wherein the bend is substantially 90 degrees.

23. The system according to claim 22, wherein the target includes a viewing aperture defining a viewing axis.

24. The system according to claim 18, wherein the means for tracking the plurality of position signaling devices is a localizer.

25. The system according to claim 24, wherein the means for processing information tracked is a computer system.

26. A method of determining an attribute of a microscope comprising the steps of:
   focusing the microscope on an object in a field of view of the microscope;
   positioning a target that includes visual indicating means for indicating when the indicating means is aligned with the focal axis of the microscope;

observing the visual indicating means through the microscope;

aligning the visual indicating means with the focal axis of the microscope; and sensing the position of the target in relation to the microscope.

27. The method according to claim 26, wherein the target includes a viewing aperture defining a viewing axis and wherein the step of positioning the target on the object includes the step of:

aligning the microscope with the viewing axis such that at least a portion of the object is viewable through the viewable aperture.

28. The method according to claim 26, wherein the target is coupled to an end of a tool head of a surgical tool.

29. A method of calibrating a microscope in an image guided surgery system, comprising the steps of:

focusing the microscope on an object of interest;

positioning a target having means for indicating a rotational sense of the target in contact with an object of interest viewed by the microscope such that the means for indicating the rotational sense of the target is aligned with a desired rotational sense of the microscope;

aligning the view of the microscope with the means for indicating the rotational sense of the target; and using the image guided surgery system to determine a position of the target and calibrate the microscope.

30. The method according to claim 29, wherein the target is coupled to an end of a tool head of a surgical tool.

* * * * *